US006610857B2

(12) United States Patent
Wolber et al.

(10) Patent No.: US 6,610,857 B2
(45) Date of Patent: Aug. 26, 2003

(54) PROCESS FOR THE PRODUCTION OF DITHIAZOLYL DISULFIDES

(75) Inventors: Wolfgang Wolber, Bergheim (DE); Markus Oberthür, Dormagen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/011,453

(22) Filed: Nov. 6, 2001

(65) Prior Publication Data
US 2002/0055640 A1 May 9, 2002

(30) Foreign Application Priority Data

Nov. 8, 2000 (DE) .......................................... 100 55 219

(51) Int. Cl.$^7$ ............................................ C07D 277/78
(52) U.S. Cl. ...................................... 548/158; 548/186
(58) Field of Search .................. 548/158, 186

(56) References Cited

U.S. PATENT DOCUMENTS

| 4,463,178 A | | 7/1984 | Tazuma ....................... 548/158 |
| 4,482,720 A | * | 11/1984 | Kaplan et al. .............. 548/158 |
| 6,124,467 A | * | 9/2000 | Nolte et al. ................. 548/158 |

FOREIGN PATENT DOCUMENTS

| CA | 1292990 | 12/1981 |
| DE | 2743629 | 3/1978 |
| DE | 23 49 314 | 5/1994 |
| EP | 0 194 571 A1 | 9/1986 |
| GB | 1379871 | 1/1975 |

OTHER PUBLICATIONS

Repkina V.I.; Ptitsyna V.V.; Latysheva L.M.; J. Appl. Chem. USSR (Engl. Transl.), Bd. 57, 1984, Seiten 1082–1084, XP001037091 *das ganze Dokument*.

Repkina V.P., Ptitsyna V.V and Latysheva L.M.: "oxidation of 2–mercaptobenzothiazole by hydroogen peroxyde in dilute aqueous solutions" J. Appl. Chem. USSR, Bd. 57, 1984, Seite 180–181 XP001038637 *das ganze Dokument*.

Seto S. et al.: Bull. Chem. Soc. Japan, Bd. 35, 1962, Seiten 1998–2002, XP001038439 *das ganze Dokument*.

Kirk–Othmer, Encyclopedia of Polymer Science and Technology (month unavailable) 1970, vol. 12, pp. 262–263, Mercaptothiazoles and Derivatives.

CRC Handbook of Chemistry and Physics, 79$^{th}$ edition (month unavailable) 1988, pp. 8–43, Buffer Solutions Giving Round Values of pH at 25° C.

* cited by examiner

*Primary Examiner*—Robert Gerstl
(74) *Attorney, Agent, or Firm*—Joseph C. Gil; Jennifer R. Seng; Noland J. Cheung

(57) ABSTRACT

The invention relates to a process for the production of 2,2'-dithiazolyl disulfides by oxidation of 2-mercaptothiazoles with peroxidic compounds in an aqueous suspension in a specific pH range.

6 Claims, No Drawings

PROCESS FOR THE PRODUCTION OF DITHIAZOLYL DISULFIDES

FIELD OF THE INVENTION

The invention relates to a process for the production of 2,2'-dithiazolyl disulfides by oxidation of 2-mercaptothiazoles with peroxidic compounds in an aqueous suspension in a specific pH range.

BACKGROUND OF THE INVENTION

In the industrial production of dibenzothiazyl disulfides by oxidation of 2-mercaptobenzothiazoles, many different oxidizing agents have already been used (Ullmanns Encyclopedia of Industrial Chemistry, $5^{th}$ ed. vol. A-26, p. 773–8, VCH, Weinheim, Basel, Cambridge, New York, Tokyo, 1995). Thus, oxidation with sodium chlorate and sodium nitrite solution in a hydrochloric acid medium at 30° C. is prior art. However, this process has a series of disadvantages. The consumption of mineral acid is very high (3 moles of HCl per mole of 2-mercaptobenzothiazole) and large quantities of co-products are formed. It is also known to perform the oxidation of 2-mercaptobenzothiazoles using nitrous acid. According to the process of U.S. Pat. No. 1,908,935, 2-mercaptobenzothiazole is suspended in water, a water-soluble nitrite is added and oxygen or an oxygen-containing gas, such as air, is passed through the reaction mixture. At the same time a mineral acid, which releases nitrous acid from the nitrite, is added. In the process according to U.S. Pat. No. 2,119,131 and U.S. Pat. No. 3,062,825, stoichiometric quantities of nitrite are used as the sole oxidizing agent. As a result, a more rapid and more complete reaction is achieved. These oxidation processes are also disadvantageous in so far as the consumption of mineral acid is again very high here, and salts and nitrogen oxides are formed in large quantities as by-products.

Chlorine has also been used as an oxidizing agent (Kirk-Othmer, Encyclopedia of Polymer Science and Technology (1970), vol. 12, p. 262). However, this is a complicated reaction with critical reaction conditions in which large quantities of superoxidized by-products are often formed. According to DE-A 23 09 584, to increase the product yield and reduce the quantity of excess chlorine required for adequate oxidation, separate streams of an aqueous solution of an alkali metal salt of mercaptobenzothiazole, an aqueous solution of an alkali metal hydroxide and gaseous chlorine are continuously reacted with one another under the surface of the liquid, with vigorous stirring, at 20 to 75° C., the pH and the redox potential of the aqueous mixture being kept at pH 7 to 10 and a redox potential of −150 to 250 mV by regulating the feed of the aqueous hydroxide solution and the gaseous chlorine. This process also requires very careful control in order to prevent the further oxidation of dibenzothiazyl disulfide to benzothiazyl-2-sulfinate and -sulfonate. The process is also disadvantageous because large quantities of alkali hydroxide are consumed and large quantities of common salt are formed as a co-product.

Hydroperoxides, such as hydrogen peroxide, alkyl hydroperoxides and aralkyl hydroperoxides, have also already been used as oxidizing agents in the production of dibenzothiazyl disulfide (cf. e.g. DE-A 23 49 314). However, the use of a low aliphatic alcohol as solvent is expressly required here. The use of organic solvents is disadvantageous for an industrial process, however, since they can represent both an environmental hazard and, owing to their high inflammability, a constant fire hazard. In addition, organic solvents have to be recycled, purified and disposed of after use, which is expensive.

The oxidation of heterocyclic thiols to disulfides with the aid of hydrogen peroxide or organic peracids in water or organic solvents or in mixtures thereof is described in EP-A 194 571 A1. However, no specific pH which must imperatively be adhered to during these reactions is disclosed therein. In the examples there is only a single reaction in an aqueous medium, in which, however, the thiol is reacted in great dilution (2% solution) and in a homogeneously dissolved form, with hydrogen peroxide. In this way, which is described herein, a very large quantity of water is required in the reaction and a correspondingly large quantity of wastewater is produced, which must be disposed of at great cost. No possibility of working heterogeneously in concentrated suspension, thus saving solvent or wastewater, is disclosed.

This possibility of reacting 2-mercaptothiazoles with hydroperoxides, especially with hydrogen peroxide, in concentrated aqueous suspension is described in U.S. Pat. No. 4,463,178. According to this publication, however, the use of an aqueous amine solution, such as e.g. ammonia or alkylamine solution, is explicitly required as a solubility promoter for the otherwise water-insoluble 2-mercaptothiazole. It is not disclosed that the oxidation reaction can take place without any problems and with quantitative yields even without any solubility-promoting auxiliary agent in pure water.

EP-A 008 548 describes the use of hydrogen peroxide as an oxidizing agent in combination with ethylenediaminetetraacetic acid or the salts thereof. The reaction times have to be very long here, over 24 hours in some cases, to achieve complete conversion. This is a great disadvantage for a large-scale process.

Common to all the above-mentioned oxidation processes is the disadvantage that comparatively expensive oxidizing agents, together with acids, bases, solvents or other auxiliary substances, are required and, in some cases, unusable co- or by-products are also formed.

A process for the electrolytic oxidation of 2-mercaptobenzothiazole to dibenzothiazyl disulfide should also be mentioned (cf. DE-A 27 43 629). This process is technically complex and therefore less economical.

SUMMARY OF THE INVENTION

There is still, therefore, a need to create an improved process for the oxidation of 2-mercaptothiazoles by means of peroxidic compounds.

Therefore, the present invention provides a process for the production of 2,2'-dithiazolyl disulfides of the general formula

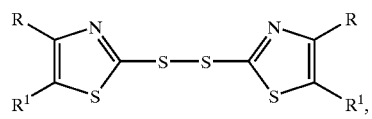

wherein

R and $R^1$ can be the same or different and each denote hydrogen, halogen, nitro, hydroxyl or optionally substituted $C_1$–$C_{12}$ alkyl or alkoxyl or $C_6$–$C_{12}$ cycloalkyl or aryl or $C_1$–$C_{12}$ heteroaryl, or jointly form the residue

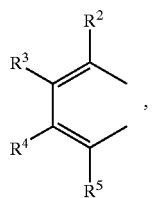

wherein
R² to R⁵ have the same meaning as R and R¹, by oxidation of a corresponding substituted 2-mercaptothiazole with peroxidic compounds, characterized in that the oxidation is performed in an aqueous suspension at a pH in the range of 6.5 to 8.0.

DETAILED DESCRIPTION OF THE INVENTION

The present invention relates to a process for the production of 2,2'-dithiazolyl disulfides of the general formula

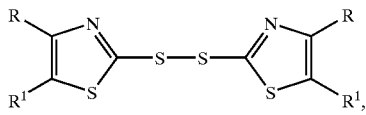

wherein
R and R¹ can be the same or different and each denote hydrogen, halogen, nitro, hydroxyl or optionally substituted $C_1$–$C_{12}$ alkyl or alkoxyl or $C_6$–$C_{12}$ cycloalkyl or aryl or $C_1$–$C_{12}$ heteroaryl, or jointly form the residue

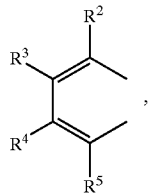

wherein
R² to R⁵ have the same meaning as R and R¹, by oxidation of a corresponding substituted 2-mercaptothiazole with peroxidic compounds, characterized in that the oxidation is performed in an aqueous suspension at a pH in the range of 6.5 to 8.0, preferably 6.8 to 7.5.

In the above formula, fluorine, chlorine, bromine or iodine, preferably chlorine or bromine, are suitable as halogen residues.

$C_1$–$C_{12}$ alkyl is understood to mean all linear or branched alkyl residues with 1 to 12 C atoms known to the person skilled in the art, such as methyl, ethyl, n-propyl, i-propyl, n-butyl, i-butyl, t-butyl, n-pentyl, i-pentyl, neo-pentyl and hexyl, which, for their part, can, in turn, be substituted. Suitable substituents in this case are halogen, nitro, hydroxyl, or else $C_1$–$C_{12}$ alkyl or alkoxy, and $C_6$–$C_{12}$ cycloalkyl or aryl, such as benzoyl, trimethyl phenyl, ethyl phenyl, chloromethyl, chloroethyl and nitromethyl.

$C_1$–$C_{12}$ alkoxyl is understood to mean all linear or branched alkoxyl residues with 1 to 12 C atoms known to the person skilled in the art, such as methoxy, ethoxy, n-propoxy, i-propoxy, n-butoxy, i-butoxy, t-butoxy, n-pentoxy, i-pentoxy, neo-pentoxy and hexoxy, which, for their part, can, in turn, be substituted. Suitable substituents in this case are halogen, nitro, hydroxyl or else $C_1$–$C_{12}$ alkyl or alkoxyl, and $C_6$–$C_{12}$ cycloalkyl or aryl.

$C_6$–$C_{12}$ cycloalkyl is understood to mean all mono- or polynuclear cycloalkyl residues with 6 to 12 C atoms known to the person skilled in the art, such as cyclohexyl, cycloheptyl, cyclooctyl and cyclononyl, which, for their part, can, in turn, be substituted. Suitable substituents in this case are halogen, nitro, hydroxyl or else $C_1$–$C_{12}$ alkyl or alkoxyl, and $C_6$–$C_{12}$ cycloalkyl or aryl, such as methylcyclohexyl, chlorocyclohexyl and nitro-cyclohexyl.

$C_6$–$C_{12}$ aryl is understood to mean all mono- or polynuclear aryl residues with 6 to 12 C atoms known to the person skilled in the art, such as phenyl or naphthyl, which, for their part, can, in turn, be substituted. Suitable substituents in this case are halogen, nitro, hydroxyl or else $C_1$–$C_{12}$ alkyl or alkoxyl, and $C_6$–$C_{12}$ cycloalkyl or aryl, such as bromophenyl, chlorophenyl, toluyl and nitrophenyl.

$C_1$–$C_{12}$ heteroaryl is understood to mean all mono- or polynuclear heteroaryl residues known to the person skilled in the art which, in addition to 1 to 12 C atoms, also contain one or more heteroatoms, such as N, S, O and/or P, in the aromatic ring system, such as pyridinyl, triazinyl, furyl, thienyl, thiazolyl, thiazinyl, pyrrolyl, quinolinyl which, for their part, can, in turn, be substituted by the above-mentioned substituents.

The residues R–R⁵ in the formula preferably denote hydrogen, methyl, ethyl, propyl, t-butyl, methoxy, ethoxy, cyclohexyl, benzoyl, methoxy, ethoxy, phenyl, naphthyl, chlorophenyl, toluyl and nitrophenyl.

2,2'-Dithiazolyl disulfides are used e.g. as vulcanizing agents for rubber. The process according to the present invention is particularly significant for the production of 2,2'-dibenzothiazolyl disulfide, a most preferred embodiment of this class of compounds. However, it is also suitable and successful in the production of other compounds of this type. For the preferred production of 2,2'-dibenzothiazolyl disulfide (MBTS), 2-mercaptobenzothiazole (MBT) is used as the starting substance. Examples of other 2-mercaptothiazoles that are suitable as starting substances for the production of other 2,2'-dithiazolyl disulfides of the general formula (I) include the compounds mentioned in DE-A 23 55 897, such as 2-mercaptothiazole
2-mercapto-4-methylthiazole
2-mercapto-4-ethylthiazole
2-mercapto-4-n-propylthiazole
2-mercapto-4-n-butylthiazole
2-mercapto-4,5-dimethylthiazole
2-mercapto-4,5-di-n-butylthiazole
2-mercapto-4-phenylthiazole
2-mercapto-5-chloro-4-phenylthiazole
2-mercapto-4-p-bromophenylthiazole
2-mercapto-4-m-nitrophenylthiazole
2-mercapto-4-m-chlorophenylthiazole
2-mercapto-4-methylbenzothiazole
2-mercapto-5-methylbenzothiazole
2-mercapto-6-methylbenzothiazole
2-mercapto-4,5-dimethylbenzothiazole
2-mercapto-4-phenylbenzothiazole
2-mercapto-4-methoxybenzothiazole
2-mercapto-6-methoxybenzothiazole
2-mercapto-5,6-dimethoxybenzothiazole
2-mercapto-6-methoxy-4-nitrobenzothiazole 2-mercapto-6-ethoxybenzothiazole
2-mercapto-4-chlorobenzothiazole
2-mercapto-5-chlorobenzothiazole
2-mercapto-6-chlorobenzothiazole
2-mercapto-7-chlorobenzothiazole
2-mercapto-5-chloro-6-methoxybenzothiazole
2-mercapto-5-chloro-4-nitrobenzothiazole
2-mercapto-5-chloro-6-nitrobenzothiazole
2-mercapto-4,5-dichlorobenzothiazole
2-mercapto-4,7-dichlorobenzothiazole
2-mercapto-5-nitrobenzothiazole
2-mercapto-6-nitrobenzothiazole
2-mercapto-4-phenylbenzothiazole
2-mercapto-naphthothiazole
2-mercapto-6-hydroxybenzothiazole.

As mentioned, peroxidic compounds, especially hydrogen peroxide, alkyl hydroperoxides or aralkyl hydroperoxides, are used as oxidizing agents. Naturally, mixtures of these can also be used. All peroxides described in DE-A-2 349 314 can be used as alkyl hydroperoxides and aralkyl hydroperoxides. However, hydrogen peroxide is preferred. In general, the peroxide concentration used in the process according to the present invention is in the range of 3 to 50 wt %. For economic reasons, peroxide concentrations of 5 to 35 wt % are preferably used, more preferably, 10 to 35 wt %.

Water is used as the solvent for the process according to the present invention. However, water-miscible organic solvents that are stable to oxidation can also be added to the water. Examples of these are alcohols and ketones, dimethylformamide and acetone, and mixtures thereof. Suitable alcohols are e.g. aliphatic alcohols with 1 to 10 carbon atoms, especially methanol, ethanol, propanol, isopropanol, n-butanol, sec.-butanol, tert.-butanol, pentanol, hexanol, heptanol and octanol. The concentration of the solvent in the water is not critical. In general, the quantity of solvent is in the range of 1 to 10 wt %, based on the quantity of water. Larger quantities of solvent should be avoided for economic reasons, since in these cases, larger quantities of solvent also have to be processed or disposed of.

Naturally, it is also possible to produce or release the peroxides, especially hydrogen peroxide, in situ from suitable precursors.

The pH of the process according to the present invention must imperatively lie within the range stated from beginning to end of the reaction. If it falls below this range, the yield and purity of the end product are reduced. If the pH range is exceeded, the yield and selectivity of the reaction are reduced and by-products are formed which pass into the end product and also into the wastewater. As a result, the product according to the present invention is contaminated and the wastewater polluted with organic material.

In order to prevent pH fluctuations during the reaction and to keep the reaction precisely within the pH range specified, an efficient measurement and control technique can be used, consisting e.g. of an in situ pH measurement and an electronically controlled metering system for the acid or base to be added as required.

Suitable acids and bases are known to the person skilled in the art; their selection is not critical. Acids preferably used are e.g. sulfuric, hydrochloric or phosphoric acid. Preferred bases are e.g. aqueous solutions of ammonium hydroxide or of basic metal hydroxides from groups 1 to 13 of the periodic table, preferably sodium hydroxide or potassium hydroxide.

In order to be able to compensate very rapidly, even for smaller pH fluctuations, a buffer system is preferably used, adapted to the required pH range. Suitable buffers for this purpose are known to the person skilled in the art and can be found e.g. in "Römpp Chemie Lexikon", Thieme Verlag Stuttgart, $9^{th}$ edition, vol. 5, (1992) 3677 or in the "CRC Handbook of Chemistry and Physics" $79^{th}$ ed. (1998) 8–43.

For example, buffers can be used which are composed of a mixture of metal hydrogen carbonates and metal carbonates, or of a mixture of metal hydrogen phosphate and metal phosphate, the metals coming from groups 1 to 13 of the periodic table, and e.g. of a mixture of nitrogen-containing bases, such as triethanolamine, tris(hydroxymethyl)aminomethane or imidazole and their ammonium salts, formed by reaction with an acid, e.g. hydrochloric acid or sulfuric acid. The components of the buffer, e.g. the metal salts mentioned, can be used individually or mixed together.

Buffers composed of a mixture of sodium or potassium salts with anions of hydrogen carbonate and carbonate, or of dihydrogen phosphate, hydrogen phosphate and phosphate, or of tris(hydroxymethyl)aminomethane and its ammonium salts, are preferably used.

The buffer can be used both as the only pH control and, preferably, in combination with an efficient regulating system as described above.

The quantity of buffer used and the corresponding buffer capacity depend on the strength of the pH fluctuation to be expected, which is, in turn, dependent on the reaction conditions, such as temperature and rate of metering and the efficiency of the pH regulating system used, and can readily be determined by appropriate preliminary tests.

The reaction temperature in the process according to the present invention is about 0 to 150° C., preferably 20 to 90° C. and more preferably 30 to 70° C. At lower temperatures, the rate of reaction decreases, and at higher temperatures the selectivity of the reaction is reduced.

The reaction period is generally 0.5 to 10 hours under the above reaction conditions.

The process according to the present invention is performed in a simple manner, e.g. in that the 2-mercaptothiazole is dispersed in the reaction medium in powdered form, a buffer is optionally added, dissolved or in solid form, and the hydrogen peroxide is allowed to flow in under the pressure and temperature conditions stated, preferably with stirring.

In the process according to the present invention, practically quantitative yields and selectivities of more than 98% are achieved. The 2,2-dithiazolyl disulfides obtainable are distinguished by high purity and can be used directly as rubber vulcanizing agents, for example, without further purification.

The 2,2'-dithiazolyl disulfides that can be produced according to the present invention are excellently suited as vulcanization accelerators in sulfur-containing rubber mixtures. Dibenzothiazyl disulfide is especially suitable.

EXAMPLES a) In a double-walled, thermostatically controlled 2-liter flat-flange beaker, fitted with a pH measuring electrode with control technology connected for two metering pumps, thermometer, agitator, dropping funnel and baffle, a suspension of 169 g (1 mol) 2-mercaptobenzothiazole in 1,700 ml water was adjusted to pH 7.18 with 500 ml of buffer solution, under inert gas ($N_2$), and heated to 40° C. with stirring. The buffer solution was prepared by dissolving 15.14 g (12.5 mmol) tris(hydroxymethyl)aminomethane in 250 ml water, adding 210 ml 0.1 mol/l hydrochloric acid and topping up the solution to 500 ml with water. Within 6 h, 600 ml of a dilute, aqueous hydrogen peroxide solution (0.525 mol H₂O₂) were added to the reaction mixture, stirring and keeping the pH in the range of 7 to 7.5 by means of control technology with two metering pumps. For this control, a total of 350 ml 1% sodium hydroxide solution and 165 ml 2% sulfuric acid were required. On completion of the dropwise addition, the test for H₂O₂ (starch iodide paper) was weakly positive. Stirring was continued for 30 min at 40° C., the mixture was filtered and the product washed with water. Yield: 163.1 g (98.1% of theoretical value), content of active substance according to titration: 97.1% MBTS, m.p.: 167–171° C.

b) In a double-walled, thermostatically controlled 2-liter flat-flange beaker, fitted with a pH measuring electrode with control technology connected for two metering pumps, thermometer, agitator, dropping funnel and baffle, a suspension of 169 g (1 mol) 2-mercaptobenzothiazole in 1,700 ml water at pH 6.80 was heated to 70° C. under inert gas (N₂), with stirring. Within 6 h, 600 ml of a dilute, aqueous hydrogen peroxide solution (0.525 mol H₂O₂) were added, stirring and keeping the pH in the range of 7 to 7.5 by means of control technology with two metering pumps. For this control, a total of 230 ml 1% sodium hydroxide solution and 140 ml 2% sulfuric acid were required. On completion of the dropwise addition, the test for H₂O₂ (starch iodide paper) was weakly positive. Stirring was continued for 30 min at 40° C., the mixture was filtered and the product washed with water. Yield: 163.0 g (98.0% of theoretical value), content of active substance according to titration: 98.8% MBTS, m.p.: 169.5 to 172.5° C.

c) Comparative Example

With the test setup described above and the conditions given below, the test was repeated at a lower pH. The following parameters were established and maintained during the reaction: pH 5.0 to 5.5, temperature 40° C., 170 ml 1% sodium hydroxide solution consumed for the pH control. Yield: 162.2 g (97.5% of theoretical value), content of active substance: 69.7% MBTS, m.p.: 142.0 to 151.0° C.

d) Comparative Example

With the test setup described above and the conditions given below, the test was repeated at a higher pH. The following parameters were established and maintained during the reaction: pH 8.1 to 11.1, temperature 40° C., 40 g 10% sodium hydroxide solution consumed for the pH control. Yield: 150.6 g (90.6% of theoretical value), content of active substance: 88.5% MBTS, m.p.: 166.0 to 170.0° C.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. Process for the production of 2,2'-dithiazolyl disulfides of the general formula

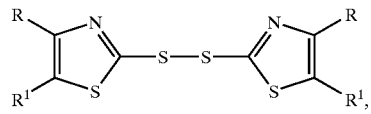

wherein

R and R¹ can be the same or different and each denote hydrogen, halogen, nitro, hydroxyl or optionally substituted $C_1$–$C_{12}$ alkyl or alkoxyl or $C_6$–$C_{12}$ cycloalkyl or aryl or $C_1$–$C_{12}$ heteroaryl, or jointly form the residue

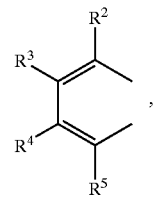

wherein

R² to R⁵ have the same meaning as R and R¹, comprising the step of oxidizing a corresponding substituted 2-mercaptothiazole with peroxidic compounds, wherein oxidation is performed in an aqueous suspension at a pH in the range of 6.5 to 8.0 and wherein the pH is within the range of 6.5 to 8.0 from beginning to end of the oxidation.

2. A process according to claim 1, wherein oxidation is performed at a pH in the range of 6.8 to 7.5.

3. A process according to claim 1, wherein said peroxidic compounds are hydrogen peroxide, alkyl hydroperoxides or aralkyl hydroperoxides.

4. A process according to claim 1, wherein said oxidizing agent is hydrogen peroxide.

5. A process according to claim 1, wherein an organic solvent that is stable to oxidation is also added to the aqueous suspension.

6. A process according to claim 1, wherein 2-mercaptothiazole is used as the 2,2'-dithiazolyl disulfide.

* * * * *